United States Patent [19]
Clayman et al.

[11] Patent Number: 5,779,698
[45] Date of Patent: Jul. 14, 1998

[54] ANGIOPLASTY CATHETER SYSTEM AND METHOD FOR MAKING SAME

[75] Inventors: Ralph V. Clayman, Clayton, Mo.; Said S. Hilal, Laguna Niguel; Michael L. Jones, Capistrano Beach, both of Calif.

[73] Assignee: Applied Medical Resources Corporation, Laguna Hills, Calif.

[21] Appl. No.: 241,007

[22] Filed: May 11, 1994

Related U.S. Application Data

[63] Continuation-in-part of Ser. No. 70,495, Jun. 2, 1993, abandoned, which is a continuation of Ser. No. 647,472, Jan. 29, 1991, abandoned, which is a continuation-in-part of Ser. No. 522,148, May 11, 1990, abandoned, which is a continuation-in-part of Ser. No. 298,477, Jan. 18, 1989, abandoned.

[51] Int. Cl.$^6$ .................................................. A61B 17/36
[52] U.S. Cl. ...................... 606/39; 604/114; 606/32; 606/45; 607/99; 607/101; 607/113
[58] Field of Search .................. 604/20, 96, 113, 604/114; 607/2, 96, 98, 99, 101, 115, 113, 116, 138, 148; 606/27–33, 45, 46, 39, 48, 50, 191–198

[56] References Cited

U.S. PATENT DOCUMENTS

| | | |
|---|---|---|
| 3,791,387 | 2/1974 | Itoh . |
| 3,910,279 | 10/1975 | Okada et al. . |
| 4,273,128 | 6/1981 | Lary . |
| 4,311,143 | 1/1982 | Komiya . |
| 4,325,374 | 4/1982 | Komiya . |
| 4,326,530 | 4/1982 | Fleury, Jr. . |
| 4,484,597 | 11/1984 | Meno et al. . |
| 4,649,924 | 3/1987 | Taccardi . |
| 4,660,560 | 4/1987 | Klein . |
| 4,669,469 | 6/1987 | Gifford, III et al. . |
| 4,709,698 | 12/1987 | Johnston et al. . |
| 4,747,405 | 5/1988 | Leckrone . |
| 4,793,348 | 12/1988 | Palmaz . |

(List continued on next page.)

FOREIGN PATENT DOCUMENTS

| | | |
|---|---|---|
| 3519626 | 12/1986 | Germany . |
| 599802 | 3/1978 | U.S.S.R. . |
| 938977 | 6/1982 | U.S.S.R. . |

OTHER PUBLICATIONS

"Catheter–Based Flexible Circuits Developed", *Medical Product Manufacturing News*, Mar. 1994.

"Electroplating and Sputtering", *Modern–Plastics Encyclopedia* 1984–85., pp. 372–374, author Gerald Krulik.

"Embossing" by Don Parr, *Modern Plastics Encyclopedia* 1984–1985, pp. 386–387.

"Parylene" brochure for Nova Tran Corporation, Clear Lake, Wisconsin.

Banning G. Lary, MD, et al. "Myocardial Revascularization Experiments Using the Epicardium", *Arch. Surg.*, 98:60–72, 1969.

(List continued on next page.)

*Primary Examiner*—Michael Powell Buiz
*Assistant Examiner*—Ronald K. Stright, Jr.
*Attorney, Agent, or Firm*—Richard L. Myers

[57] ABSTRACT

An angioplasty catheter for increasing the patency of a body vessel by altering an obstruction in the body vessel includes an elongate shaft having a proximal end and a distal end. At least one electrical conductor is disposed at the distal end and movable from a low profile position to a high profile position in proximity to the obstruction. A non-distensible balloon disposed between the conductor and the shaft is inflatable from the proximal end of the shaft to move the conductor between the low profile position and the high profile position. In the high profile position the conductor can be electrosurgically energized to ablate the obstruction and thereby increase the patency of the body vessel. The conductor may include a circuit which is printed on the exterior surface of the balloon. An overlying insulation layer can be provided with a slot to limit the exposure of the conductor to the obstruction thereby increasing the current density in the electrosurgical procedure.

13 Claims, 4 Drawing Sheets

U.S. PATENT DOCUMENTS

| | | |
|---|---|---|
| 4,799,479 | 1/1989 | Spears . |
| 4,919,133 | 4/1990 | Chiang . |
| 4,952,357 | 8/1990 | Euteneuer . |
| 4,976,711 | 12/1990 | Parins et al. . |
| 5,045,056 | 9/1991 | Behl .................................... 607/113 |
| 5,053,044 | 10/1991 | Mueller et al. . |
| 5,080,660 | 1/1992 | Buelna . |
| 5,195,965 | 3/1993 | Shantha ................................ 604/114 |
| 5,196,024 | 3/1993 | Barath . |
| 5,277,201 | 1/1994 | Stern ..................................... 607/98 |
| 5,443,470 | 8/1995 | Stern et al. ........................... 607/99 |
| 5,492,529 | 2/1996 | Neuwirth et al. .................... 604/114 |
| 5,499,981 | 3/1996 | Kordis .................................. 607/116 |

OTHER PUBLICATIONS

Banning G. Lary, MD. "Coronary artery resection and replacement by a blood conduit", Surgery, 65:584–589, 1969.

Banning G. Lary. M.D.. "An Epicardial Purse String Suture for Closing Coronary Arteriotomy". Am. Surg., 33:pp. 213–214, 1967.

Banning G. Larry M.D., et al.. A Method for Creating a Coronary–Myocardial Artery:, vol. 59: 1061–1064, 1966.

Banning G. Lary. M.D.. "Method for Increasing the Diameter of Long Segments of the Coronary Artery". Amer. Surg., 32:33–35, 1966.

Banning G. Lary MD, "Coronary Artery Incision and Dilation". Arch Surg., vol. 115, Dec. 1980. pp. 1478–1480.

Banning G. Lary MD, et al.. "Experimental Vein Angioplasty of the Circumflex Coronary Artery". Journal of Surgical Research 17, pp. 210–214, 1974.

Banning G. Lary. MD. "A Method to Create and Correct Stenosis of a Coronary Artery". Arch. Surg., vol. 93, pp. 828–830, 1966.

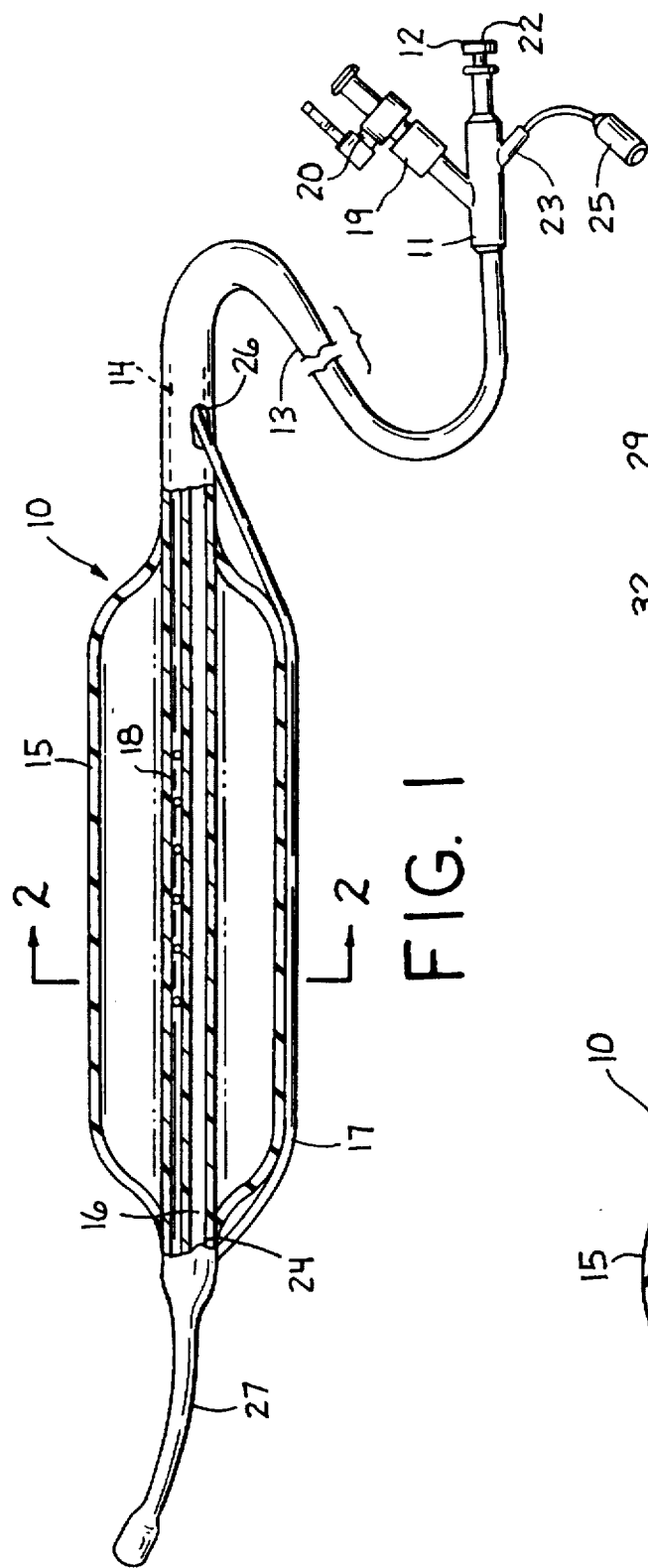
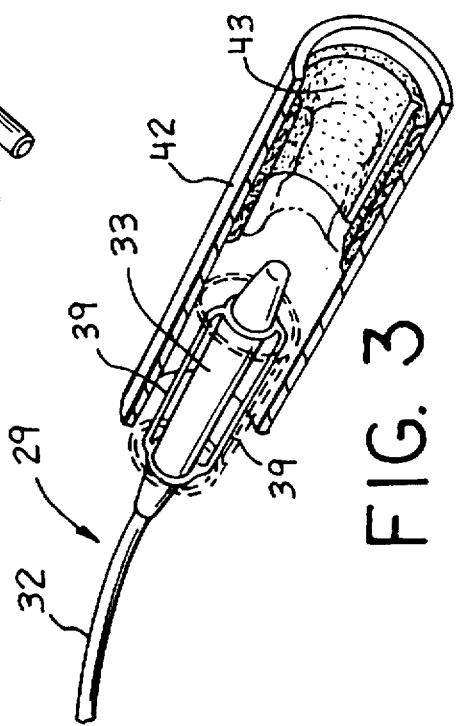
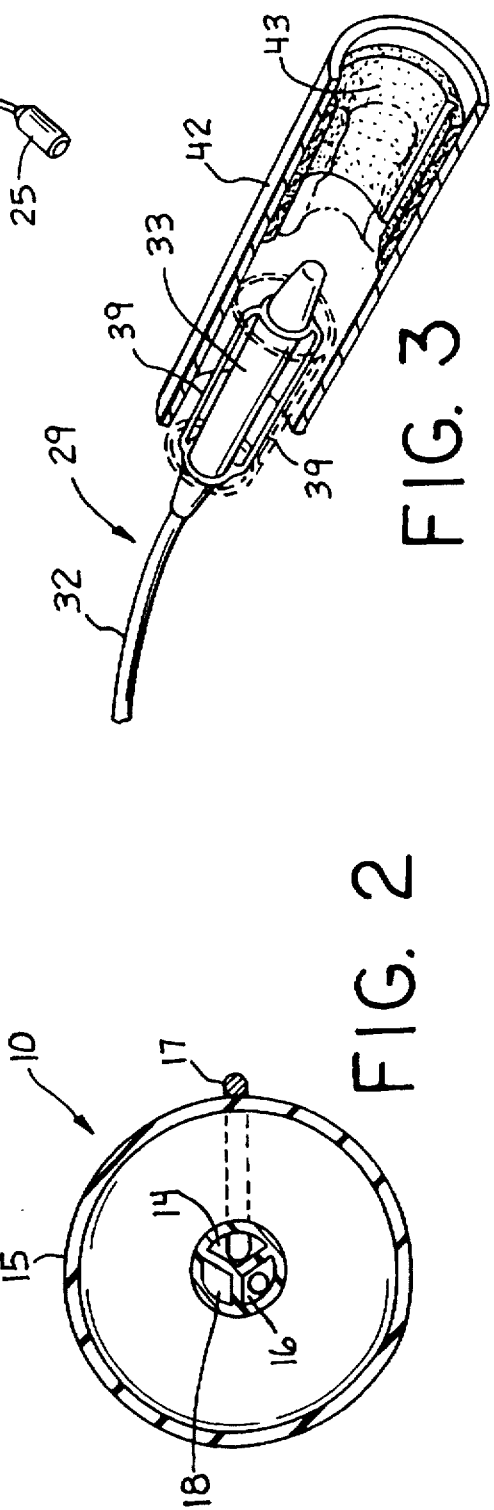

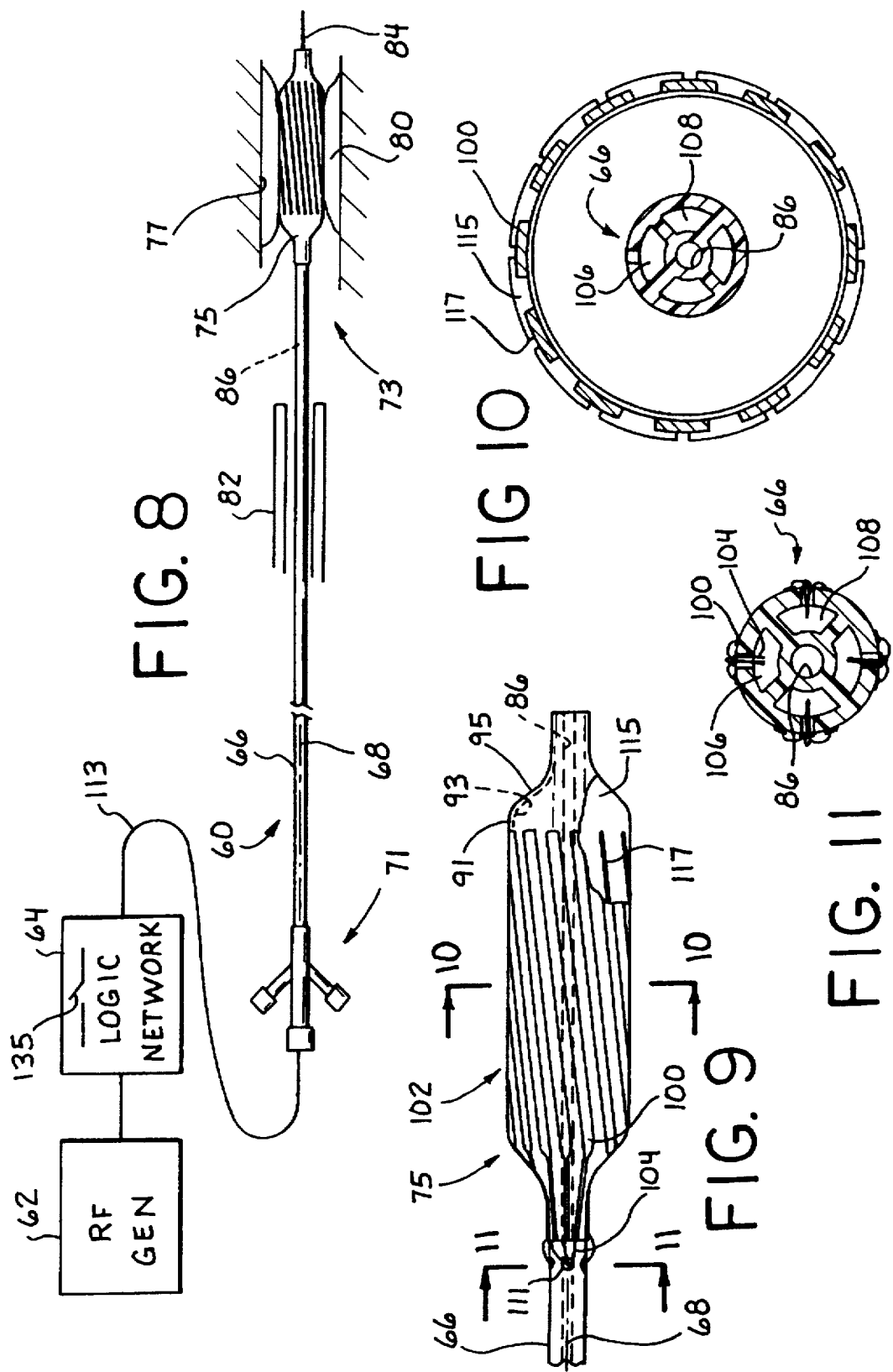

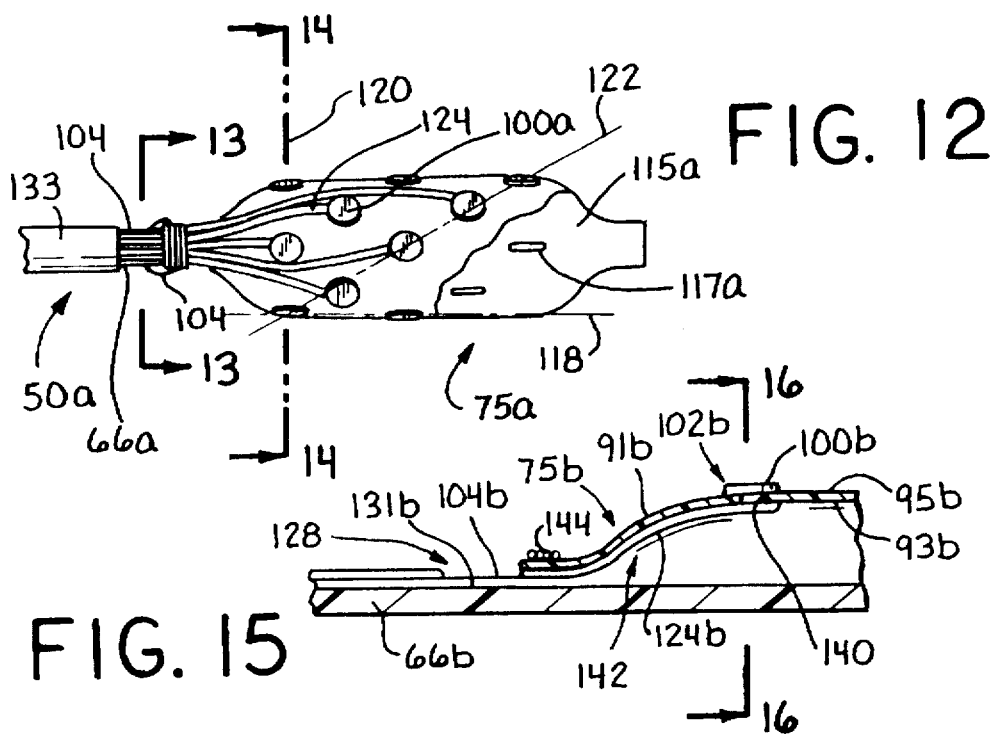
FIG. 12
FIG. 15
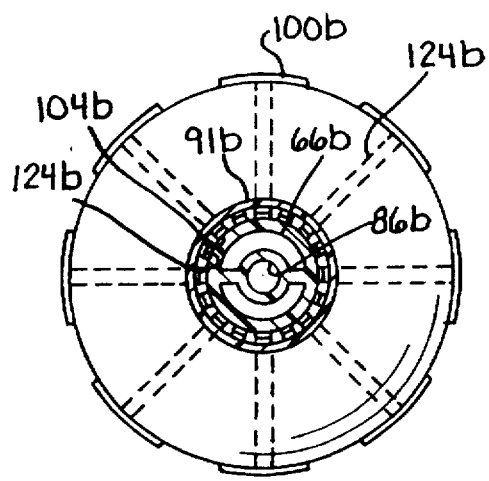
FIG. 16
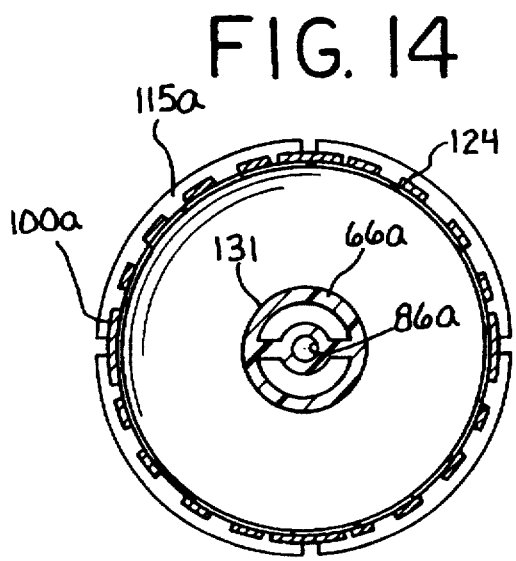
FIG. 14
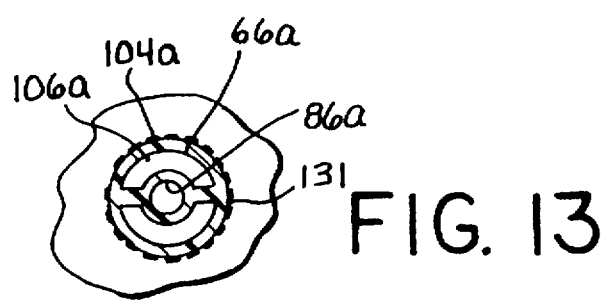
FIG. 13

ANGIOPLASTY CATHETER SYSTEM AND METHOD FOR MAKING SAME

CROSS-REFERENCE

This application is a Continuation-In-Part of application Ser. No. 08/070,495 filed on Jun. 2, 1993, now abandoned, which is a Continuation of application Ser. No. 07/647,472 filed on Jan. 29, 1991, now abandoned, which is a Continuation-In-Part of application Ser. No. 07/522,148, filed on May 11, 1990, now abandoned, which is a Continuation-In-Part of application Ser. No. 07/298,477, filed Jan. 18, 1989, now abandoned.

TECHNICAL FIELD

The present invention relates generally to the field of surgical devices and more specifically to angioplasty devices adapted to alter occlusive plaque in body vessels.

BACKGROUND OF THE INVENTION

In radiofrequency electrosurgical cutting a radiofrequency current is allowed to pass from an active cutting electrode through a patient's tissue and into a grounding pad or cable. The current cuts tissue at the active cutting electrode, the cutting rate being dependant on current density through the tissue in that area. With a low current density, heat is generated but no cut is achieved. With a high current density, fast cutting occurs.

Current density depends upon the voltage applied to the electrosurgical circuit and the series impedance or resistance to current flow of that circuit. Current density is also dependent upon the area the active cutting electrode presents to the patient's tissue. The smaller this area, the higher the current density. Since the area of the active electrode is fixed for a specific cutter, and the series impedance of the circuit is beyond the surgeon's control, the current density is typically adjusted by varying the voltage applied to the electrode. This adjustment is typically present on conventional electrosurgical generators.

The series impedance is dependent upon several factors which are outside the control of the surgeon. These factors may include the material and design of the active electrode, the type of tissue to be cut, and the location of the grounding pad relative to the cutting site. Generators used in this type of surgery have a wide range of power outputs to accommodate a variety of procedures and devices. For example, the generator can be adjusted to either cut tissue or to merely cauterize previously cut or torn tissue.

The objective in electrosurgical cutting is to heat the cells of the tissue so rapidly that they explode into steam leaving a cavity in the cell matrix. The heat is meant to be dissipated in the steam and not to dry out adjacent cells. When the electrode is moved and fresh tissue is contacted, new cells are exploded and the incision is made. The current utilized in electrosurgical cutting is in the radiofrequency range and operates by jumping across an air gap to the tissue. This is commonly referred to as sparking.

An explanation of electrosurgical cutting theory can be found in the FORCE 1 Instruction Manual published by Valleylab of Boulder, Colo., on Mar. 1, 1986.

An advantage of electrosurgical cutting, particularly if it is performed utilizing a cutting electrode as disclosed in U.S. Pat. No. 5,080,660, is that overheating of adjacent tissue with accompanying desiccation and damage is limited or prevented. Thus, this procedure provides a clean cut without damage to adjacent tissue. A clean controlled cut is particularly desirable to assure that tearing does not occur in a direction away from the desired orientation of the cut.

Dilatation catheters are used to dilate body vessels, orifices and conduits such as an artery narrowed by atherosclerotic plaque or a urethra constricted by an enlarged prostate. These catheters basically consist of an elongate cannula having an inflatable non-extensible balloon or bladder at or near its distal end. A guide wire or other axial support means is often included to improve the torque control or "steerability" of the catheter.

The major advantage of using a dilatation catheter instead of conventional surgery is that it is less invasive. Nevertheless, the dilatation processes of the past can also result in significant trauma. As the elastomeric bladder expands, it exerts pressure on the surrounding tissue, causing the tissue to compress, deform and expand. The tissue, of course, has an inherent limit of deformability. When the dilation pressure causes the tissue to deform beyond that limit, the tissue tears apart, often to form a jagged wound.

In the past, balloon catheters have been used to address arterial obstruction in a procedure commonly referred to as angioplasty. In this case, the balloon functions primarily as a compression device. The catheter is inserted into the vessel until the balloon is even with the obstruction or plaque. At this point, the balloon is inflated. It was originally thought that this inflation of the balloon compressed the plaque against the interior wall of the vessel. More recent studies have shown, however, that very little compression actually occurs. The vessel is actually torn during inflation of the balloon and the plaque is forced into the tears of the vessel thus causing an enlargement of the internal diameter. This procedure has been relatively ineffective because restenosis has occurred in a large majority of the cases. It is now known that this restenosis occurs because of the traumatic injury caused by the tearing of the vessel. In those cases where restenosis occurs, the complex surgery must be repeated.

In other cases, laser angioplasty catheters have been used to vaporize the plaque in order to increase the patency of the vessel. These catheters have been required to shield or otherwise distinguish the vessel wall from the plaque in order to avoid laser damage to the vessel. Complex laser systems have also been required to energize this type of catheter.

SUMMARY OF THE INVENTION

The present invention overcomes these deficiencies of the past making electrosurgical procedures available for increasing the patency of conduits such as blood vessels. Electrosurgery offers many advantages to such a procedure.

Particularly in the case of electrosurgical angioplasty, cutting of the vessel is accomplished in a very controlled, limited, atraumatic and accurate procedure. This results in a larger diameter for the vessel without the excessive injury and trauma which invites restenosis.

In one aspect of the invention an angioplasty catheter is adapted to increase the patency of a body vessel by ablating an obstruction in the vessel. The catheter includes an elongate shaft extending along a central longitudinal axis between a proximal end and a distal end. This shaft has a length sufficient to extend from a percutaneous insertion site to an operative site at the location of the obstruction in the vessel. At least one electrical conductor is disposed at the distal end of the shaft, the conductor being movable from the low profile position in proximity to the axis of the shaft to a high profile position in proximity to the obstruction at the operative site. Means operable at the proximal end of the shaft moves the conductor between the low profile position and the high profile position. The conductor is electrosurgically energized in the high profile position at the operative site to ablate the obstruction and thereby increase the patency of the body vessel.

In another aspect of the present invention, a balloon catheter is provided with a printed circuit on the exterior surface of the balloon. This electrical circuit can include discrete areas of electrically conductive material which form the second electrode of an electrosurgical circuit. When the balloon is inflated, the printed circuit is moved into close proximity with the material defining the body conduit. When this printed circuit is energized a pattern of incisions is formed to increase the patency of the body conduit. The printed circuit can be formed with a minimal depth so that the overall increase in the diameter of the balloon is negligible. Accordingly, the balloon can be maintained in a very low profile which is particularly preferred in coronary angioplasty procedures.

The printed circuit on the balloon can be formed by vacuum deposition in accordance with methods better known to those skilled in the art of electronic chip design. The exterior surface of the balloon can be masked with voids having the shape of the desired printed circuit. Vacuum deposition through the voids will print the circuit on to the balloon. A similar masking technique can be used to form an insulative layer over the printed circuit. This insulative layer can be provided with slits which control the density of current flowing from the conductive areas of the printed circuit. This insulation layer also functions to provide the desired spacing between the printed circuit and the tissue to be cut.

In another aspect of the invention, an electrosurgical catheter is adapted to increase the patency of a body conduit, and comprises an elongate shaft extending along a central longitudinal axis between a proximal end and an opposing distal end. Portions of this shaft define an inflation lumen which extends through the shaft. A nondistensible balloon is disposed at the distal end of the shaft in fluid communication with the inflation lumen. This balloon has an interior surface facing toward the axis of the shaft and an exterior surface facing away from the axis of the shaft.

A printed circuit is disposed on the exterior surface of the balloon and includes a plurality of discrete areas of electrically conductive material. Means for conducting electrical energy is disposed to extend from the proximal end of the shaft to the areas of conductive material at the distal end of the shaft. This energy conductive means is coupled to the areas of conductive material in the printed circuit in order to electrosurgically energize the circuit. This permits the catheter to be inserted into the body conduit where the discrete areas can be energized to electrosurgically remove the material defining the body conduit and thereby increase the patency of the body conduit.

A second printed circuit can be formed on the shaft of the catheter in the form of a plurality of conductors. These conductors of the second printed circuit are electrically coupled to the discrete areas of the first printed circuit. A third circuit can be printed on the interior surface of the balloon to form a plurality of strips which extend through the wall of the balloon into electrical contact with the discrete areas of the first electrical circuit. In such an embodiment, the first electrical circuit is energized through the conductors of the second electrical circuit and the strips of the third electrical circuit. Logic means can be provided for selectively energizing the discrete areas of the first printed circuit in a predetermined patterned which permits the material to be cut along different lines in order to increase the patency of the body conduit.

In another aspect of the invention, a method for making an electrosurgical catheter includes the steps of providing an elongate shaft having a central longitudinal axis and an inflation lumen extending between a proximal end and an opposing distal end. A balloon material can also be provided with an interior surface and an exterior surface. This exterior surface of the balloon material can then be printed with an electrical circuit including a plurality of discrete areas of electrical conductive material. The balloon material can then be attached to the shaft in fluid conductive relationship with the inflation lumen to form an inflatable balloon at the distal end of the shaft. A plurality of discrete conductors can then be provided along the shaft and coupled to the discrete areas of the circuit.

This process produces a catheter which can then be energized with an electrosurgical signal at its proximal end in order to energize the discrete areas of the printed circuit on the balloon. The printed circuit can be formed by providing in close proximity to the exterior surface of the balloon a mask having voids in the shape of a circuit. Depositing the electrical conductive material through the voids of the mesh and on to the exterior surface of the balloon forms the circuit. Then the mask can be removed from the balloon leaving the conductive material on the exterior surface of the balloon in the shape of the circuit.

A second electrical circuit can be printed on the shaft to form discrete conductors which extend along the shaft into electrically conductive relationship with the first printed circuit. A third printed circuit can also be printed on the interior surface of the balloon to form a plurality of electrically conductive strips each extending in an electrically conductive relationship between the first printed circuit and the second printed circuit.

In a further aspect of the invention, a method for increasing the patency of the body conduit includes the step of providing an electrosurgical catheter with a shaft and an inflatable balloon having an interior surface and an exterior surface. The balloon also carries on its exterior surface a printed circuit having a plurality of discrete areas of electrically conductive material. This catheter can be inserted into the body conduit until the balloon reaches a predetermined location. Inflating the balloon through the shaft radially expands the balloon and carries the printed circuit into close proximity with the body conduit at the predetermined location. Energizing the discrete areas of the printed circuit in a predetermined pattern removes material defining the body conduit to increase the patency of the body conduit.

These and other features and advantages of the invention will become more apparent with a description of preferred embodiments and reference to the associated drawings.

BRIEF DESCRIPTION OF THE DRAWINGS

The invention will be better understood with reference to the drawings wherein like numbers denote like parts and wherein:

FIG. 1 is a partly cross-sectional, isometric view of one embodiment of the invention catheter;

FIG. 2 is a cross-sectional view taken along line 2—2 of FIG. 1;

FIG. 3 is a perspective, schematic, sectional view of a portion of another embodiment of the invention illustrating the catheter positioned within a body conduit;

FIG. 8 is a schematic view of one embodiment of the present invention including an electrosurgical generator, a logic network, and a catheter;

FIG. 9 is a side view of the catheter partially in phantom and illustrating a printed circuit on the exterior surface of a balloon;

FIG. 10 is a radial cross section view taken along lines 10—10 of FIG. 9;

FIG. 11 is a radial cross section view taken along lines 11—11 of FIG. 9;

FIG. 12 is a side elevation view similar to FIG. 9 and showing an additional embodiment of the catheter of the present invention;

FIG. 13 is a radial cross section view taken along lines 13—13 of FIG. 12;

FIG. 14 is a radial cross section view taken along lines 14—14 of FIG. 12;

FIG. 15 is an axial cross section view of a further embodiment of the catheter of the present invention; and FIG. 16 is a radial cross section view taken along lines 16—16 of FIG. 15.

Figure 4:
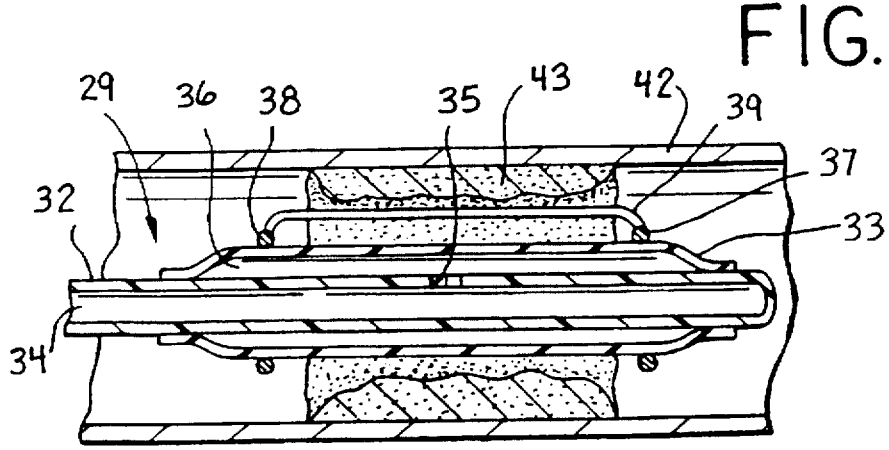
FIG. 4 is a sectional, side view of the embodiment of FIG. 3 in a deflated state.
Figure 5:
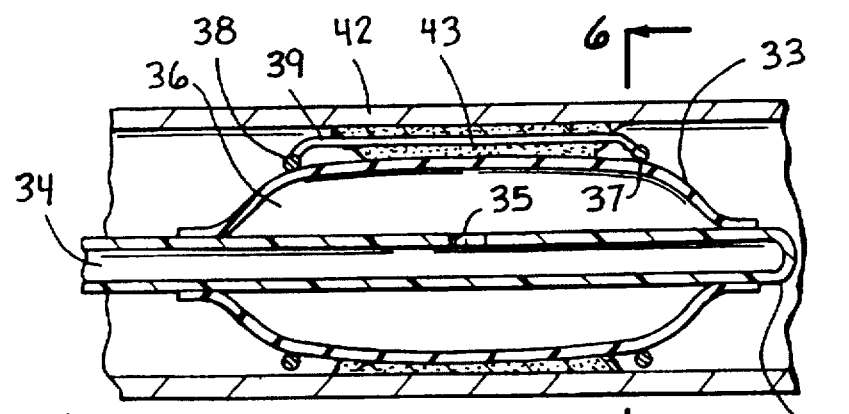
FIG. 5 is a sectional side view of the embodiment of FIG. 3 in an inflated state.

DESCRIPTION OF PREFERRED EMBODIMENTS AND BEST MODE FOR CARRYING OUT THE INVENTION

FIG. 1 depicts a dilatation catheter assembly, generally designated 10, that may be used for dilating a body vessel or conduit, such as a ureter or urethra, to treat a blockage or other obstruction. The main elements of catheter assembly 10 are: an adapter 11 that defines the proximal end 12 of the assembly 10 and a site for various ports to the assembly 10; a catheter body 13 having a triple lumen 14 (FIG. 2); an inflatable balloon or bladder member 15; a stiffening guide wire or stylet 16 that extends longitudinally within one of the three lumens 14 of the catheter body 13; and a cutting element or electrode 17, preferably a radiofrequency cutting element 17 activatable by a radiofrequency power source 21. The electrosurgical cutting element 17 can be the nature of a wire which extends generally parallel to the longitudinally extending inflatable bladder 15.

In use, the bladder 15 is inserted into a body conduit vessel or orifice to a location where a surgical cut is required. The bladder 15 is then inflated (an inextensible bladder is generally used) with radiofrequency current being passed through the cutting element 17. This leads to the wire being moved outwardly and incising adjacent tissue in that direction.

The material used for the wire can be any of the materials currently used for electrosurgical cutting. For example, the wire can be made of stainless steel or tungsten. As illustrated in FIG. 2 herein, one of the three lumens 14 serves as an inflation/deflation passageway 18, a second lumen carries the guidewire or stylet 16 and serves as a drainage/infusion passageway, and a third lumen carries the cutting element 17. In accordance with the teachings in previously mentioned copending patent application Ser. No. 07/522,254, a sheath surrounding the cutting element 17 can be provided with a slit facing away from the bladder 15.

In accordance with the present invention the inflatable balloon or bladder member 15 is preferably of the inextensible or constant volume variety, that is it can, when expanded, assume only a specific size and shape. Thus, the balloon member 15 cannot extend or bulge longitudinally within the body conduit beyond its predetermined diameter or length. Since a nondistensible balloon member 15 cannot extend longitudinally, as can elastic or elastomeric balloons, it must exert the force caused by inflation of the balloon member 15 radially against an enclosing body conduit or the like. In contrast, if an elastic or elastomeric balloon is expanded within a body conduit which has one portion particularly narrowed and particularly resistant to expansion, the balloon will simply elongate rather than acting radially outwardly against the constriction.

In accordance with the present invention it is preferred to utilize a radiofrequency cutting element 17 for a number of reasons. One reason is that a radiofrequency cutting element 17 will not perform any cutting unless and until it is activated by passing a radiofrequency current through it. As a result, accidental cuts cannot be made away from the area where cutting is desired. And second, with proper control, cutting can be very sharply defined leading to a clean incision without tearing. This radiofrequency cutting or cauterizing technique can, thus, provide significant advantages over the use of prior art cutters in an apparatus of the nature disclosed herein.

The balloon member 15 generally extends longitudinally along the body conduit and is generally symmetrically placed and expandable therein. In this manner, as the balloon member 15 is expanded, it exerts a substantially equal tangential tension upon the tissue defining the body conduit. This results in a very clean incision which extends generally parallel to the balloon member 15. In this manner the incision can be positioned longitudinally along the body cavity rather than at an axial angle as might be the case if the tangential tension in the body conduit were not substantially uniform.

In a preferred embodiment the cutting element 17 is a radiofrequency cutting element and is disposed parallel to the bladder member 15. This bladder member 15 extends longitudinally along the body conduit, is constructed of an inextensible non-elastic, non-elastomeric material and is symmetrically placed within the body cavity so that on expansion it exerts a substantially uniform tangential tension upon the tissue defining the body cavity. This configuration achieves many of the advantages associated with the present invention.

The adapter 11 serves as a site for a bladder inflation/deflation port 19 that is attached to a source of inflation medium (not shown) for inflating the bladder member 15, or to a suction source (not shown) for deflating the bladder member 15. Port 19 has a valve 20 for regulating the inflation medium or suction, as the case may be. Port 19 connects into the proximal end of an inflation/deflation passageway 18 that extends from the port 19 to the bladder member 15. The adapter 11 also serves as a site for the drainage tube inlet/outlet port 22 and a cutting element port 23. The drainage port 22 is connected to the proximal end of the lumen that carries the guide wire or stylet 16. The drainage port 22 may serve as a site for removing fluid from the lumen or as a site for infusing fluid into the lumen.

The distal end of the catheter body has a series of drain holes 24 to facilitate flushing the lumen with fluid or voiding the bladder member 15. A "banana plug" cutting element connector 25 is affixed to the end of the cutting element port. The cutting element 17 extends from the connector 25 through the lumen of the catheter body 13, exits therefrom via an aperture 26, and continues along the exterior of the bladder member 15.

In this particular embodiment, the cutting element 17 can consist of a thin wire which has an external incising edge that faces outwardly from the bladder member 15. Alternatively, the cutting element 17 may be a sharp edge, beam, or, more preferable, a radiofrequency cutting or cauterizing element 17. The element 17 and bladder member 15 are constructed such that the cutting element 17 is carried on the exterior of the bladder member 15 (at least when the bladder member is inflated) but is not capable of incising the bladder member 15.

If desired, the portion of the exterior of the bladder member 15 that is exposed to the cutting element 17 may carry a protective cover (not shown) to further guard against the bladder member 15 being incised by the cutting element 17. The cutting element 17 may be carried at a predetermined spacing from the bladder surface or directly on the surface. When carried on the surface the cutting element 17 may be an integral part of the surface or may be attached to the surface. In a preferred embodiment, the cutting element 17 is manually extendable or retractable via the connector 25 into and out of the catheter body 13.

For use in urethral dilatation the distal end of the assembly 10 includes a coudet tip 27. Such structure may not be necessary or desirable for dilating other conduit/orifices. For urethral dilation, the assembly 10 may optionally include another lumen and "Foley" type balloon (not shown) distally of the dilatation bladder member 15 to anchor the catheter in the bladder neck of the human body and thereby facilitate correct positioning of the dilatation bladder member 15. This has the further advantage of minimizing the possibility of migration and displacement of the assembly 10. One or more of the catheter assembly components may be made of radiopaque materials to facilitate the visualization of the assembly 10 by the physician during placement of the assembly 10 in the body vessel/conduit.

The typical surgical procedure in which the catheter assembly 10 is employed, involves the following steps. Normally a guidewire is first inserted into the vessel/conduit/orifice to be dilated. Calibration devices may be guided over the guidewire to facilitate measuring the extent of the vessel/conduit/orifice being dilated. The dilatation catheter of FIG. 1 is then inserted to the desired depth in the vessel/conduit and positioned using fluoroscopic and/or x-ray techniques.

Once in position, the bladder member 15 is inflated. Such inflation causes the cutting element 17 to move radially outwardly as the bladder surface expands radially until the cutting element 17 contacts the surrounding tissue. As used herein the term "tissue" is intended to include, without limitation, normal tissue, neoplastic tissue (tumors) or an obstruction such as plaque. In accordance with a preferred embodiment of the invention the bladder member 15 is nondistensible.

Continued radial expansion of the bladder member 15 positions the cutting element 17 and causes the bladder member 15 to exert pressure on the tissue thereby subjecting the tissue to a substantially uniform tangential tension. Then a radiofrequency current can be passed through the cutting element 17.

This alternating cutting and dilating action results in the tissue being expanded without being torn due to a buildup of excess stresses within the tissue. Instead, the tissue is cut in a clean, concentrated, generally longitudinal fashion by the cutting element 17 and the dilatation does not uncontrollably tear the tissue and cause excessive trauma and bleeding. The inflated bladder member 15 provides the additional benefit of acting as a tamponade to reduce bleeding.

After the vessel/conduit/orifice tissue is incised and dilated, and the blockage/obstruction is relieved, the power through the radiofrequency cutting element 17 is discontinued. Then the bladder member 15 can be deflated by operation of the inflation/deflation port valve 20. Deflation of the bladder member 15 permits a simultaneously radial retraction of the cutting element 17 out of contact with the tissue. As the bladder member 15 is deflated the cutting element 17 may be retracted via the connector 25. If desired, the cutting element 17 may be retracted prior to complete deflation of the bladder member 15 and/or the bladder member 15 reinflated and left in place to act as a tampon. Alternatively, the catheter can be withdrawn from the vessel/conduit altogether.

FIGS. 3–6 depict another dilatation catheter assembly of the invention, designated generally by the reference numeral 29. Only the distal end of the assembly 29 is shown. The adapter(s), as well as the various inflation/deflation ports are not shown for convenience. The distal end of the catheter is defined by a closed end catheter tube 32 which carries an inflatable, preferably inextensible, bladder member 33 on its exterior. The lumen 34 of the tube 32 is connected to the source of inflation fluid pressure/suction, as the case may be. The tube 32 has a radial aperture 35 that opens into the lumen 36 of the bladder member 33. A pair of expandable ring-shaped members 37, 38 extend around the exterior of the bladder member 33 near the distal and proximal ends thereof. One or more cutting elements 39 are affixed between the rings so that they extend longitudinally and outwardly therefrom.

FIG. 3 (in solid line) and FIG. 4 both show the assembly 29 in its deflated state positioned within a vessel 42 partially occluded by an obstruction 43. In order to inflate the bladder member 33, pressurized fluid is passed through catheter tube lumen 34 and aperture 35 into the bladder lumen. Inflation of the bladder member 33 in turn causes the ring members 37, 38 to expand and move the cutting element(s) 39 radially outward. FIGS. 3 (phantom line), 5, and 6 show the bladder member 33 in an inflated state with the cutting element 39 incising the obstruction.

Figure 7:
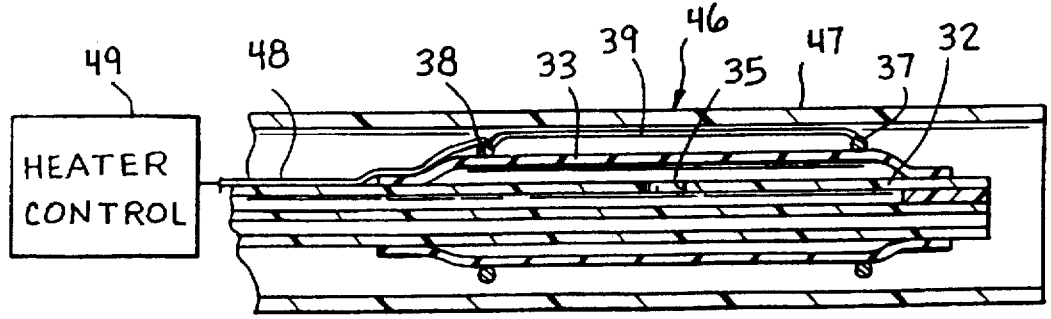
FIG. 7 is a sectional, elevational view of another embodiment of the invention.
Figure 6:
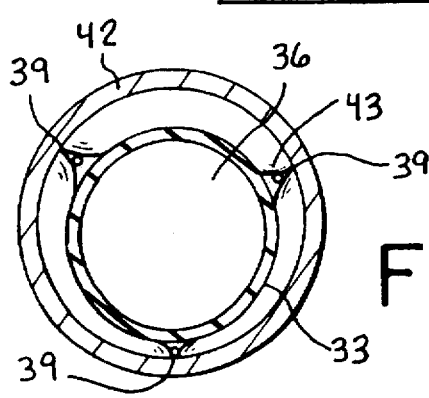
FIG. 6 is a cross-sectional view along line 6—6 of FIG. 5.

FIG. 7 shows yet another dilatation catheter assembly, generally designated 46, of the invention. The assembly 46 is shown in its deflated state. This assembly 46 is similar in structure to assembly 29 except that the assembly 46 is housed within a sheath or introducer 47 and a cauterizing element 48 is connected to the cutting element 39. The sheath permits the assembly 46 to be introduced into the vessel in an unexposed manner, ejected from the end thereof for use, and retracted back into the sheath 47 after use. The ejection and retraction may be achieved by relative longitudinal movement of the sheath 47, assembly 46, or both.

A heating element permits the cutting element (which in this instance must be made of a heat conducting material) to be heated to a temperature which allows the tissue to be both incised and cauterized. The heating element is included in a heat source/control, schematically shown at 49. As an alternative the cutting element 39 can be a radiofrequency cutting element and cauterization will result along with the cutting. Also, following cutting a reduced power radiofrequency signal can be passed through cutting element 39 to accomplish further cauterization. In such an embodiment, the heat source control 49 would be replaced by a radiofrequency signal generator.

A catheter of the present invention is illustrated in FIG. 8 and designated generally by the reference numeral 60. This catheter 60 is adapted for use in an electrosurgical catheter system which includes a radiofrequency generator 62 and a logic network 64 described in greater detail below. The catheter 60 includes a shaft 66 which extends along a central axis 68 between a proximal end 71 and a distal end 73. At the distal end 73, a balloon 75 is fixed to the shaft 66 of the catheter 60.

This catheter 60 is particularly adapted for use in increasing the patency of body conduits. Such conduits may include the urinary track, the vascular system and particularly the coronary arteries. Whether these body conduits are defined by living tissue or by non-living deposits, they can become restricted significantly decreasing the fluid flow through the conduit. This is particularly true in the case of body conduits such as the blood vessel 77 illustrated in FIG. 8. These vessels, which are relied on to facilitate a flow of blood, are commonly blocked by plaque 80 which forms on the intimal lining of the vessel 77. This plaque occurs in both peripheral and coronary arteries, and typically consists of calcium, fibroblasts, and cholesterol. In all cases, the plaque 80 is undesirable as it tends to obstruct the flow of blood through the vessel 77. In a procedure commonly referred to as angioplasty, balloon catheter have been used to press this plaque against the intimal lining of the vessel 77. In this procedure which does not contemplate removal of the plaque 80, restenosis of the vessel 77 commonly occurs.

In accordance with the present invention, radiofrequency power is applied to the plaque 80 or other obstruction of the body conduit, in an electrosurgical procedure. This procedure actually reduces the volume of the plaque 80 so that the stenosis of the vessel 77 is less obstructive. In a typical angioplasty procedure, a guide catheter 82 is inserted into the vascular system and toward the vessel 77. A guidewire 84 can then be introduced through the guide catheter 82 and into the vessel 77. It is of particular advantage if the guidewire 84 can be passed through the plaque 80 or other occlusion in the body conduit.

The shaft 66 of the catheter 60 is commonly formed with a central guidewire lumen 86 extending along at least a portion of the shaft 66. This lumen 86 which exits the catheter 60 at the distal end 73 is threaded onto the guidewire 84 interiorly of the guide catheter 82 and exteriorly of the guidewire 84 until the balloon 75 is disposed adjacent the occlusion or plaque 80. At this predetermined location, the balloon 75 can be inflated and the RF generator 62 activated to remove the plaque 80 in a manner described in greater detail below.

The construction of the balloon 75 is of particular interest to the present invention. Referring to the enlarged view of FIG. 9, it is apparent that the balloon 75 has a wall 91 which is defined by an interior surface 93 and an exterior surface 95. The material of the balloon 75 is preferably nondistensible so that the wall 91 is not stretched but rather maintains a generally constant area. When the balloon 75 is not inflated, this wall 91 is collapsed and highly wrinkled in a low profile state. When the balloon 75 is inflated, the wall 91 achieves its maximum predetermined radius in a high profile state. In a preferred embodiment, the balloon is formed from polyethylene.

Disposed on the exterior surface 95 of the balloon 75 are a plurality of discrete pads 100 of electrically conductive material which form a printed circuit 102. These pads 100 are formed on the exterior surface 95 preferably in a vacuum deposition process which provides the pads 100 with a minimum thickness. This greatly reduces the radial profile of the balloon 75. The pads 100 are not interconnected but rather are electrically separated so that they are capable of being individually or collectively energized. As illustrated in FIG. 9, a preferred embodiment of the catheter 60 includes a plurality of the pads 100 arranged in lines extending along the length of the balloon 75 transverse to the axis 68 in a generally parallel relationship.

A plurality of conductors 104, extend along the shaft 66 each in an electrically conductive relationship with an associated one of the pads 100. These conductors 104 extend from the pads 100 along the shaft 66 to the proximal end 71 of the catheter 60. By energizing the conductors 104, the discrete pads 100 also become energized to facilitate electrosurgical cutting at the balloon 75.

In the embodiment of FIG. 9, the conductors 104 are discrete wires which run interiorly of the shaft 66 from the proximal end 71 toward the distal end 73. In this embodiment, the shaft 66 is formed with not only the guidewire lumen 86 but also an inflation lumen 106, and perhaps additional lumens 108 for other purposes such as medication delivery. The inflation lumen 106 will typically exit the shaft 66 beneath the balloon 75 thereby permitting the balloon 75 to be inflated from the proximal end 71 of the catheter 60.

One of the other lumens 108 or perhaps the inflation lumen 106, can be used to house the conductors 104 interiorly of the shaft 66. A plurality of holes 111 formed in the wall of the shaft 66 proximally of the balloon 75 enables each of the conductors 104 to exit the shaft 66 and make electrical contact with the associated pad 100. In this embodiment, each of the conductors 104 passes exteriorly of the shaft 66 through one of the holes 111 and is soldered or otherwise electrically coupled to an associated one of the pads 100 which form the printed circuit 102 on the exterior surface 95 of the balloon 75. At the proximal end 71, the conductors 104 are bundled in a cable 113 which is connected through the logic network 64 to the generator 62. Power from the generator 62 is selectively introduced into the conductors 104 to energize the pads 100 of the printed circuit 102.

As disclosed in U.S. Pat. No. 5,080,660 entitled Electrosurgical Electrode it may be advisable to cover the pads 100 with a coating 115 of insulation. This coating 115 can be cut to form a narrow slit 117 over each of the pads 100. The area of this slit 117 can be controlled to reduce the exposure of the associated pad 100 thereby increasing the current density at each of the slits 117.

Vaporizing, cutting, incising, removing or other altering of the material, such as the plaque 80, is accomplished by the arcing of radiofrequency current from the electrode, such as the pad 100, to the material. To facilitate this arcing, it is desirable that the pad 100 not be placed in direct touching contact with the material, but rather that a slight gap be maintained between the pad 100 and the tissue. The coating 115 can be relied on for this function. By controlling the thickness of the coating 115 to a predetermined dimension, a gap is maintained between the tissue and the pads 100. This gap facilitates the desirable arcing which occurs through the slit 117. The coating 115 can be vacuum deposited over the printed circuit 102.

A further embodiment of the invention is illustrated in FIGS. 12–14. In this embodiment, structural elements which are similar to those previously discussed are designated by the same reference numeral followed by the lower case letter "a". Thus it can be seen that this embodiment of the catheter 50a includes the shaft 66a.

In this case, the pads 100a are relatively small in size and may have, for example, a circular configuration. The number and orientation of the pads is not critical to the invention. Nevertheless, it can be seen in FIG. 12 that the pads 100a can be oriented in rows, such as the row 118, columns, such as the column 120, and diagonals, such as the diagonal 122. Each of the pads 100a is electrically connected to a lead 124 which extends to the proximal end of the balloon 75a. As in the previous embodiment, the pads 100a and leads 124 can be printed on the exterior surface 95a of the balloon 75a in a vacuum deposition process. The insulation layer 115a can be similarly printed over the pads 100a and the leads 124.

In FIGS. 12–14, the shaft 66a has a different structural configuration than that previously discussed. Nevertheless, this shaft 66a, as well as the other embodiments of the shaft 66 are interchangeable with the various balloon embodiments.

In FIGS. 12–14, the shaft 66a has a guidewire lumen 86a as well as an inflation lumen 106a. No additional lumens need be provided in this catheter 50a because the conductors 104a are formed on an exterior surface 131 of the shaft 66a. These conductors 104a extend from the proximal end 71 distally to the balloon 75a. Vacuum deposition of these conductors 104a on the exterior surface 131 provides the necessary continuity along the shaft 66a without greatly increasing its radial dimension. In proximity to the balloon 75a, the conductors 104a can be soldered or otherwise electrically coupled to the leads 124 present at the proximal end of the balloon 75a. Thus the conductors 104a provide electrical continuity from the proximal end 71 of the catheter 50a to each of the pads 100a of the printed circuit 102a.

A coating 133 of insulation can be applied over the exterior surface 131 of the shaft 66a in order to insulate the conductors 104a. At the proximal end 71 of the catheter 50a, the conductors 104a can be soldered to discrete wires which form the cable 113. Energizing this cable 113 and conductors 104a through the logic network 64 enables the electrosurgical cutting to take place.

The function of the logic network 64 is of particular interest to this embodiment. This network 64 includes for each of the conductors 104a and associated pads 100a, a switch such as that illustrated in FIG. 8 and designated generally by the reference numeral 135. When the switch 135 is closed, the power provided by the generator 62 is passed through the associated conductor 104a to the associated pad 10a. Electrosurgical cutting occurs at this pad. When a particular switch 135 is opened, the power presented by the generator 12 does not pass through the logic network so the associated pad 100a is not energized. Accordingly, electrosurgical cutting does not take place at this pad. It can be seen that appropriate manipulation of the switches 135 in the logic network 64 will permit the pads 100a to be energized in a pattern, such as a line represented by the row 118, column 120, or diagonal 122. Thus cutting can occur repeatedly along a single line or along different lines to alter the plaque 80 or other obstruction in order to increase the patency of the body conduit, such as the vessel 77.

A further embodiment of the invention is illustrated in FIGS. 15–16. As in the previous embodiment, structural elements which are similar to those previously discussed are designated by the same reference numeral followed in this case by the lower case letter "b". This particular embodiment takes advantage of the fact that the wall 91b of the balloon 75b has two surfaces, the interior surface 93b and the exterior 95b. As in the previous embodiment, the pads 100b can be formed as the printed circuit 102b on the exterior surface 95b. Similarly, the conductors 104b can be formed as a second printed circuit 128 on the exterior surface 131b of the shaft 66b.

This embodiment differs from that of FIG. 12 in the provision of a plurality of holes 140 each extending through the balloon wall 91b beneath an associated one of the pads 100b. These holes permit the leads 124b to be formed on the interior surface 93b of the balloon 75b. The leads 124b extend through the holes 140 into electrical contact with the associated pad 100b. Thus the embodiment of FIG. 15 is configured with three printed circuits: the printed circuit 102b comprising the pads 100b, the second printed circuit 128 comprising the conductors 104b, and a third printed circuit 142 comprising the leads 124b.

It is of particular advantage that the leads 124b are formed on the interior surface 93b of the balloon 75b. This enables the leads 124b to be pressed into electrical conducting relationship with the conductors 104b on the exterior surface 131b of the shaft 66b. Increased pressure facilitating this electrical contacting relationship, can be provided by a plurality of windings 144 which radially compress the leads 124b against the conductors 104b.

As in the previous embodiments, the insulation layer 115b can be formed over the pads 100b on the exterior surface 95b of the balloon wall 91b. This insulation layer 115b can be provided with a plurality of the slots 117b each providing access through the layer 115b to an associated one of the pads 100b.

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. An electrosurgical catheter system adapted to increase the patency of a body conduit, comprising:
    an electrosurgical generator providing electrical energy at intensities and radio frequencies sufficient to generate electrical arcs and to ablate a material defining the body conduit;
    an electrosurgical catheter including an elongate shaft extending along a central longitudinal axis between a proximal end and a distal end;
    portions of the shaft defining an inflation lumen extending between the proximal end and the distal end of the shaft;
    a balloon disposed at the distal end of the shaft in fluid flow communication with the inflation lumen, the balloon having an interior surface facing toward the axis of the shaft, and having an exterior surface facing away from the axis of the shaft;
    a printed circuit disposed on the exterior surface of the balloon and including a plurality of discrete areas of electrically conductive material, the discrete areas of electrically conductive material being of a size and shape to receive the electrical energy from the electrosurgical generator and to deliver the electrical energy to the material defining the body conduit with a current density sufficient to define an electrical arc and to ablate the material defining the body conduit;
    a layer of insulation covering each of the plurality of discrete areas of conductive material, the layer of insulation having a plurality of slits, each slit being disposed over a respective one of the discrete areas and reducing an exposure of the respective discrete area and for maintaining a gap between the plurality of discrete areas and the material defining the body conduit, to thereby increase a current density at the respective slit;

means extending from the proximal end of the shaft for conducting the electrical energy from the electrosurgical generator to the distal end of the shaft means for electrically coupling the conducting means at the distal end of the shaft to each of the discrete areas of conductive material on the balloon; whereby the catheter can be inserted into the body conduit and the discrete areas can be energized in cause arcing between each of the energized discrete areas and the material defining the body conduit to electrosurgically alter the material defining the body conduit thereby increasing the patency of the body conduit.

2. The electrosurgical catheter system as recited in claim 1, wherein the printed circuit is a first printed circuit and the electrical energy conducting means comprises:

a second printed circuit disposed on the shaft and including a plurality of discrete conductors each extending along the shaft from the proximal end to the distal end; and wherein the electrically coupling means comprises:

means disposed between the shaft and the balloon for electrically coupling each of the conductors of the second printed circuit with an associated one of the discrete areas of conductive material of the first printed circuit.

3. The electrosurgical catheter system as recited in claim 2, wherein the plurality of conductors of the second printed circuit comprise vacuum deposited conductors on the exterior surface of the shaft; and wherein each of the discrete areas of electrically conductive material is electrically connected to the electrosurgical generator by a respective one of the vacuum-deposited plurality of conductors.

4. The electrosurgical catheter system as recited in claim 3, wherein the first printed circuit is vacuum-deposited.

5. The electrosurgical catheter system as recited in claim 4 wherein the layer of insulation comprises a vacuum-deposited layer of insulation.

6. The electrosurgical catheter system as recited in claim 1, further comprising:

logic means for selectively energizing the discrete areas of the first printed circuit in a predetermined pattern; whereby the material defining the body conduit can be electrosurgically cut along different lines to increase the patency of the body conduit.

7. The electrosurgical catheter system as recited in claim 6, wherein the discrete areas of electrically conductive material being arranged on the balloon in at least one of rows, diagonals, and columns, and the logic means being adapted to selectively energize the discrete areas of electrically conductive material along at least one of the rows, diagonals, and columns, to thereby facilitate electrosurgical cutting along at least one of the rows, diagonals, and columns.

8. The electrosurgical catheter system as recited in claim 1, wherein the balloon is nondistensible.

9. The electrosurgical catheter system as recited in claim 1 wherein each slit comprises a longitudinal slot having an axis and wherein the axis of at least two of said slits are collinear.

10. An angioplasty catheter system for increasing the patency of a body vessel by altering an obstruction in the body vessel, comprising:

an electrosurgical generator providing electrical energy at intensities and radio frequencies sufficient to generate electrical arcs to ablate material defining the body conduit;

an elongate shaft extending along a central longitudinal axis between a proximal end and a distal end, the shaft having a length sufficient to extend from a percutaneous insertion site to an operative site at the location of the obstruction in the vessel;

a printed circuit having at least one electrical conductor disposed at the distal end of the shaft and in electrical connecting with the electrosurgical generator, the printed circuit being movable from a low profile position in proximity to the axis of the shaft to a high profile position in proximity to the obstruction at the operative site;

a layer of insulation covering the printed circuit and having at lest one slit disposed over the at least one conductor for reducing an exposure of the at least one conductor and for spacing the printed circuit from direct contact with the body vessel;

means operable from the proximal end of the shaft for moving the printed circuit between the low profile position and the high profile position in proximity with the obstruction; and means for electrosurgically energizing the at least one conductor in the high profile position at the operative site to thereby generate an electric arc from the at least one conductor and through the slit to the body vessel such that the obstruction in proximity to the at least one conductor is altered.

11. The angioplasty catheter as recited in claim 10, wherein the moving means includes:

portions of the shaft defining an inflation lumen extending between the proximal end of the shaft and the distal end of the shaft;

a balloon disposed radially inwardly of the printed circuit at the distal end of the shaft in fluid flow communication with the inflation lumen of the shaft; and means for introducing an inflation medium into the inflation lumen at the proximal end of the shaft for inflating the balloon at the distal end of the shaft to move the printed circuit between the low profile position and the high profile position.

12. The angioplasty catheter as recited in claim 11, wherein the printed circuit is disposed on the exterior surface of the balloon.

13. The angioplasty catheter as recited in claim 10, wherein the means for electrosurgically energizing the at least one conductor includes means for receiving a radio frequency electrical current from the electrosurgical generator at the proximal end of the shaft and for introducing the radio frequency electrical current to the at least one conductor at the distal end of the shaft.

\* \* \* \* \*